United States Patent [19]
McFarlin, Sr.

[11] Patent Number: 5,666,961
[45] Date of Patent: Sep. 16, 1997

[54] EXPANSION INDICATOR DEVICE

[76] Inventor: Bill E. McFarlin, Sr., Rte. 4, Box 71, Williston, N. Dak. 58801

[21] Appl. No.: 492,515

[22] Filed: Jun. 20, 1995

[51] Int. Cl.⁶ .................................................... A61B 5/08
[52] U.S. Cl. ........................................... 128/721; 128/782
[58] Field of Search .................. 482/124, 1; 128/721, 128/782, 780

[56] References Cited

U.S. PATENT DOCUMENTS

| | | | |
|---|---|---|---|
| 4,846,462 | 7/1989 | Regnier et al. | 128/782 |
| 5,027,442 | 7/1991 | Taylor | 482/124 |

*Primary Examiner*—Max Hindenburg
*Assistant Examiner*—Pamela L. Wingood
*Attorney, Agent, or Firm*—Joseph J. Zito

[57] ABSTRACT

An expansion indicator device is used around a waist of a user to indicate whether a threshold amount of stomach cavity expansion is achieved as the user breathes and includes a strap, a power source, a feedback indicator and a switch assembly. The strap is fabricated from a stiff yet flexible material and is sized and adapted to be secured around the waist of the user. The feedback indicator is operative between an activation state whereby the power source is connected to the feedback indicator thereby energizing the feedback indicator and a de-activation state whereby the power source is disconnected from the feedback indicator thereby de-energizing the feedback indicator. The switch assembly interconnected to the power source and the feedback indicator and is operatively connected to the strap so that, as the user breathes, the switch assembly is operative to move between a closed condition and an opened condition. When the threshold amount of stomach cavity expansion is reached, the feedback indicator moves to the closed condition and becomes energized to the activation state. When the amount of stomach cavity expansion falls below the threshold amount, the feedback indicator moves to the opened condition and becomes de-energized to the de-activation state.

14 Claims, 3 Drawing Sheets

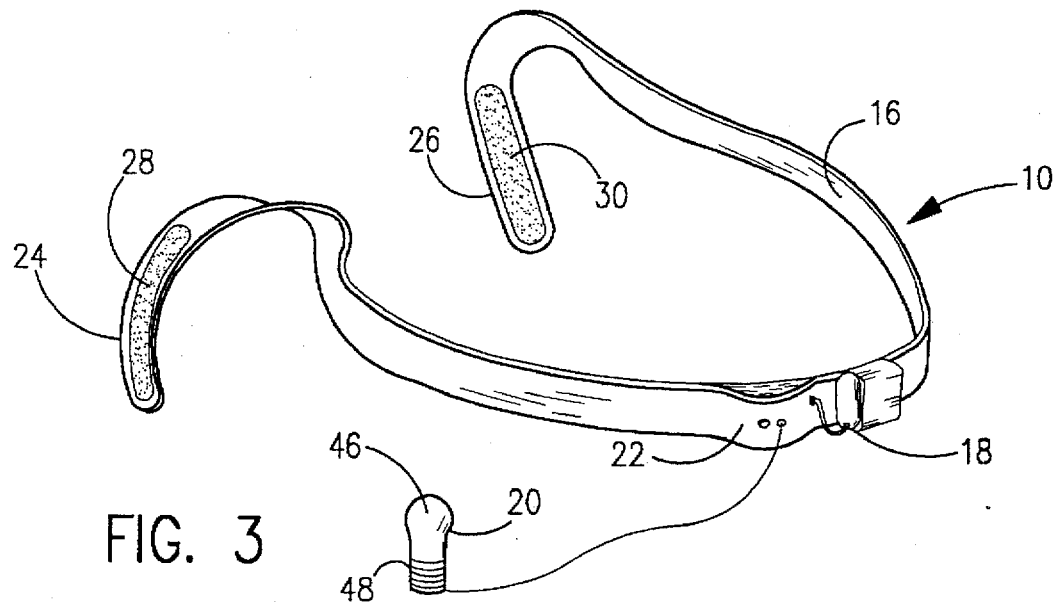
FIG. 3
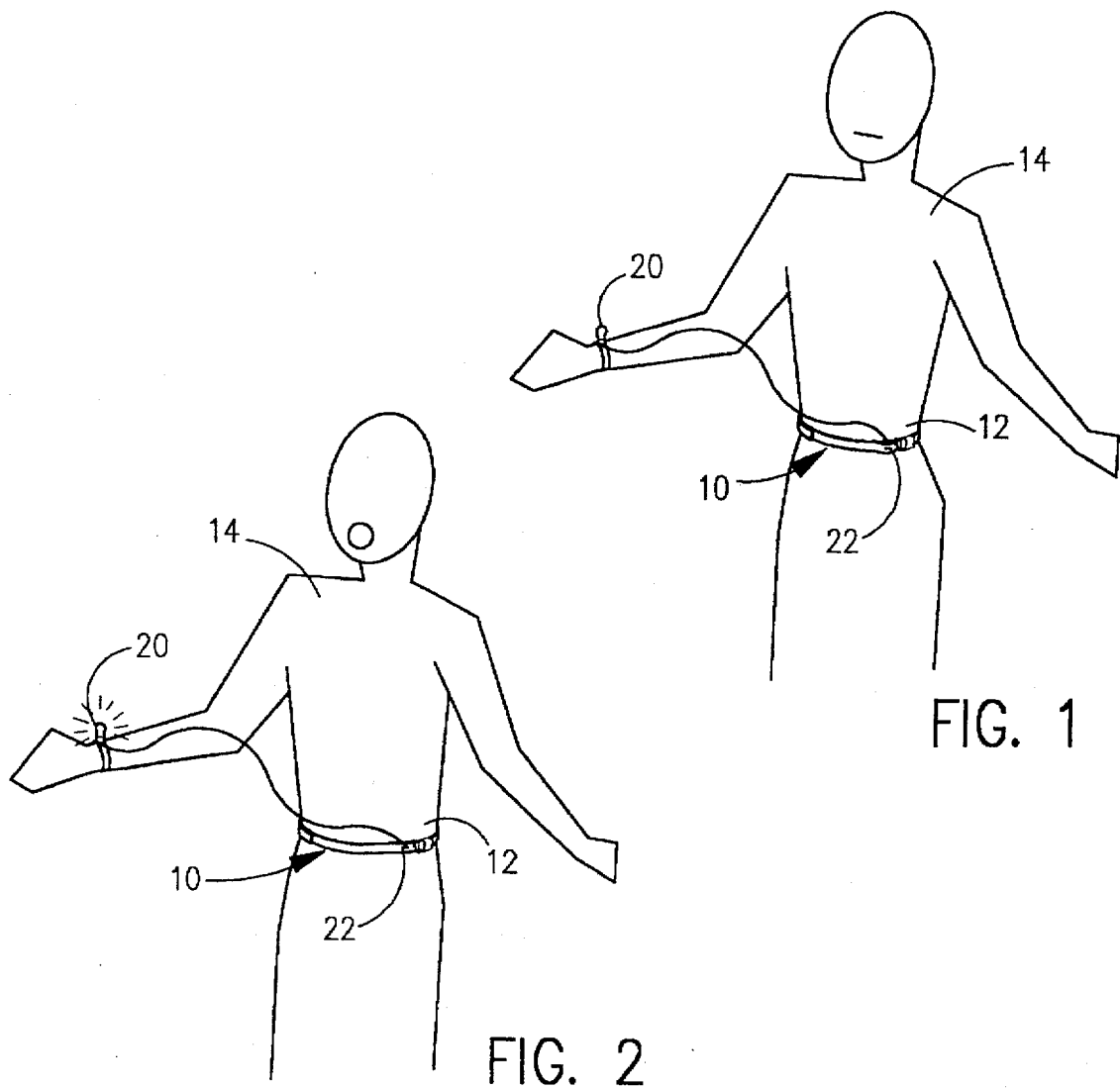
FIG. 1
FIG. 2

5,666,961

EXPANSION INDICATOR DEVICE

FIELD OF THE INVENTION

The present invention relates to an expansion indicator device which is adapted for use around an expandable body to indicate whether a threshold amount of body expansion is achieved as the body expands. More particularly, the present invention is directed to an expansion indicator device which is adapted for use around a waist of a user to indicate whether threshold amount of stomach cavity expansion is achieved as the user breathes.

BACKGROUND OF THE INVENTION

Breath control is a desirable attribute for anyone who utilizes his/her breath to project his/her voice or produce musical notes. For example, entertainers such as actors, actresses and public speakers must project their voices in order for their audiences to clearly hear their dialogue. Also, musicians playing wind instruments typically take deep breaths in order to provide adequate air from their lungs into the wind instrument to produce clear, and perhaps, long-lasting musical notes. Additionally, singers take deep breaths to produce a continuous, and often variable, melodious sound.

The accomplished entertainers and as well as teachers of entertainers are aware that, when inhaling during the breathing cycle, the entertainer's stomach cavity should expand. Proper stomach cavity expansion suggests that an adequate amount of air has been ingested for voice projection or for production of musical notes by a wind-instrument musicians and singers. Although the concept of breath control is a simple one to teach, often, however, it is difficult for a novice to practice. Presently, teachers must constantly monitor the student for appropriate breath control until it becomes sufficiently ingrained into the student to be automatic. Presently, there are no equipment or devices readily available that could be used by the student to determine by himself/herself whether he/she is practicing good breath control.

There is a need in the marketplace to provide a device so that an entertainer or student can monitor his/her stomach cavity expansion when breathing to determine if adequate breath control is taking place while practicing his/her trade. The present invention satisfies this need.

OBJECTS AND SUMMARY OF THE INVENTION

An object of the present invention is to provide an expansion indicator device which can be adapted for use around a waist of a user to indicate to the user whether a threshold amount of stomach cavity expansion is achieved as the user breathes.

Another another object of the present invention is to provide an expansion indicator device so that a user can monitor his/her own stomach cavity expansion when breathing to determine if adequate breath control is taking place while breathing.

Yet another object of the present invention is to provide an expansion indicator device employing readily available components such as a switch assembly which is simple in design and inexpensive to manufacture.

Still further, another object of the present invention is to provide an expansion indicator device which can be adapted for use around an expandable body to indicate whether a threshold amount of body expansion is achieved as the body expands.

Accordingly, an expansion indicator device of the present invention is hereinafter described. The expansion indicator device is adapted for use around a waist of a user to indicate whether a threshold amount of stomach cavity expansion is achieved as the user breathes. In its broadest form, the expansion indicator device includes a strap, a power source, a feedback indicator and a switch assembly. The strap is fabricated from a stiff yet flexible material and is sized and adapted to be secured around the waist of the user. The power source is connected to the feedback indicator which is operative between an activation state and a de-activation state. In the activation state, the power source is connected to the feedback indicator thereby energizing the feedback indicator. In the de-activation state, the power source is disconnected from the feedback indicator thereby de-energizing it.

The switch assembly is interconnected to the power source and the feedback indicator and is operatively connected to the strap. As the user breathes, the switch assembly is operative to move between a closed condition and an opened condition. The closed condition occurs when the threshold amount of stomach cavity expansion is reached and, thus, the feedback indicator becomes energized to the activation state. The opened condition occurs when the amount of stomach cavity expansion falls below the threshold amount and, thus, the feedback indicator becomes de-energized to the de-activation state.

The expansion indicator device employs a switch assembly that includes a band of stiff yet flexible material and a strip of elastic material connected together at respective ends. The band of stiff yet flexible material has a first electrode fastened thereto and the strip of elastic material has a second electrode fastened thereto. The first and second electrodes are arranged so that as the strip stretches, it draws the band towards it. When the stomach cavity expands at a predetermined amount, the first and second electrodes contact each other, which, in turn, activates the feedback indicator.

The expansion indicator device of the present invention can also be adapted for use around an expandable body to indicate whether a threshold amount of body expansion is achieved as the body expands. One example of an expandable body is a tree whereon the expansion indicator device can be secured around a tree trunk of the tree to reflect a threshold amount of tree trunk growth. Other uses of the expansion indicator device shall become apparent as the description proceeds.

These and other objects of the present invention will become more readily appreciated and understood from consideration of the following detailed description of the exemplary embodiments of the present invention when taken in conjunction with the accompanying drawings, in which:

BRIEF DESCRIPTION OF THE DRAWINGS

FIG. 1 is a perspective view of an expansion indicator device being worn around a waist of a user who has not achieved a threshold amount of stomach cavity expansion as indicated by a feedback indicator such as a light bulb being in a de-activation state, i.e. not illuminated;

FIG. 2 is a perspective view of the expansion indicator device being worn around the waist of the user who has achieved the threshold amount of stomach cavity expansion as indicated by the feedback indicator such as a light bulb being in an activation state, i.e. illuminated;

FIG. 3 is an enlarged perspective view of the expansion indicator device of the present invention shown in FIGS. 1 and 2;

DETAILED DESCRIPTION OF THE EXEMPLARY EMBODIMENTS

Figure 4:
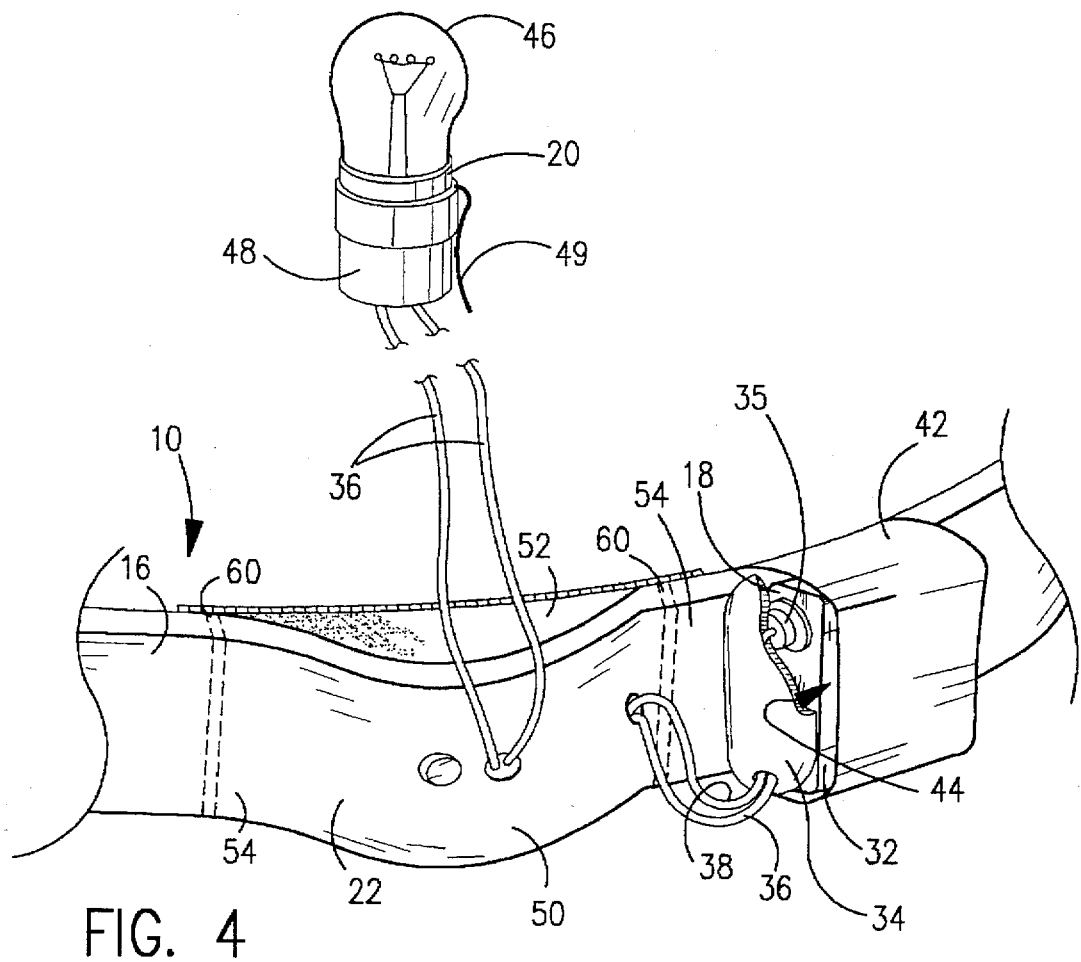
FIG. 4 is an enlarged, fragmentary perspective view of the expansion indicator device of the present invention of FIG. 1 showing a switch assembly and a power source.
Figure 5:
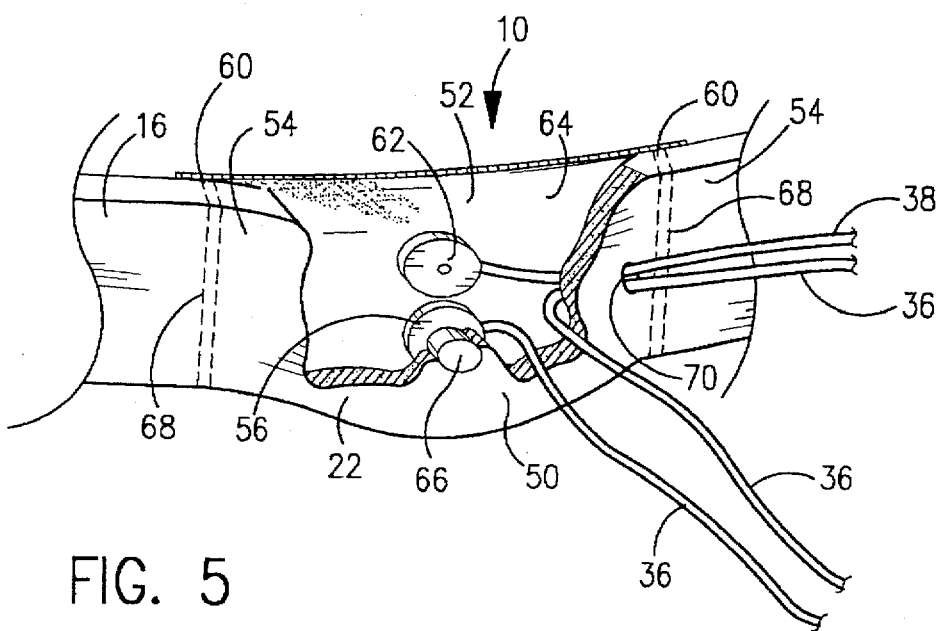
FIG. 5 is an enlarged, fragmentary perspective view of the expansion indicator device of the present invention with a partially cut-away switch assembly illustrating a first electrode and a second electrode with respective electrical connections.

An expansion indicator device of the present invention is adapted for use around a waist of a user to indicate whether a threshold amount of stomach cavity expansion is achieved as the user breathes. One of ordinary skill in the art would appreciate that the expansion indicator device of the present invention is not limited to use by a user to determine whether an appropriate amount of stomach cavity expansion has been achieved. The expansion indicator device of the present invention can be adapted for use with any expandable body to indicate whether a threshold amount of body expansion is achieved as the body expands. However, the skilled artisan would appreciate that the expansion indicator device of the present invention is not intended to determine with accuracy minute body expansion movement. Also, the expansion indicator device of the present invention can be adapted for use to determine that a threshold distance between two bodies moving linearly apart from each other has been achieved. The skilled artisan will appreciate the advantages and benefits as well as other uses of the present invention as the description proceeds.

An expansion indicator device 10 of a first exemplary embodiment of the present invention is generally introduced in FIGS. 1-8. As shown in FIGS. 1 and 2, expansion indicator device 10 is adapted for use around a waist 12 of a user 14 to indicate whether a threshold amount of stomach cavity expansion is achieved as the user breathes which is explained in further detail hereinbelow. With reference to FIG. 3, expansion indicator device 10 includes a strap 16, a power source 18, a feedback indicator 20 and a switch assembly 22. Strap 16 is fabricated from a stiff yet flexible material such as cloth, nylon, leather, imitation leather, plastic or other material typically used to fabricate straps and is sized and adapted to be secured around waist 12 of user 14 as best shown in FIGS. 1 and 2.

Feedback indicator 20 is operative in association with power source 18 and between an activation state and an de-activation state. In the activation state, power source 18 is connected to feedback indicator 20 thereby energizing feedback indicator 20. In the de-activation state, power source 18 is disconnected from feedback indicator 20 thereby de-energizing feedback indicator 20. In conjunction therewith, switch assembly 22 is electrically interconnected to power source 18 and feedback indicator 20 and is operatively connected to strap 16. Now, as user 14 breathes, switch assembly 22 is operative to move between a closed condition and an opened condition. When the threshold amount of stomach cavity expansion is reached, switch assembly 22 is in the closed condition and, as a result, feedback indicator 20 becomes energized to the activation state. It is appreciated that when feedback indicator 20 is energized to the activation state, feedback indicator 20 signals user 14 that the threshold amount of stomach cavity expansion has been reached. When the amount of stomach cavity expansion falls below the threshold amount, switch assembly 22 is in the opened condition and, as a result, feedback indicator 20 becomes de-energized to the de-activation state. Of course, when feedback indicator 20 is de-energized i.e. in the de-activation state, user 14 knows that the threshold amount of stomach cavity expansion has not been achieved.

As best shown in FIG. 3, strap 16 includes a first free end portion 24 and a second free end portion 26. First and second free end portions 24 and 26 are adapted to releasably fasten to one another. Although not by way of limitation, first free end portion 24 includes a conventional hook fastener 28 and second free end portion 26 includes a conventional loop fastener 30. However, a skilled artisan would appreciate that first free end portion 24 could include loop fastener 30 while second free end portion 26 could include hook fastener 28. Furthermore, first and second free end portions can also be releasably fastened to one another by any other conventional means such as by tying or with conventional belt buckles or conventional strap connectors. It is preferred that expansion indicator device 10 of the first exemplary embodiment of the present invention incorporate conventional hook fastener 28 and conventional loop fastener 30 so that expansion indicator device 10 could be simply and easily secured around various waste sizes of different users, thus, affording adjustability.

With reference to FIG. 4, power source 18 includes a dry cell battery 32. For example purposes only, dry cell battery 32 is a conventional 9-volt battery. A conventional battery connector element 34 is releasably connected to respective standard terminals 35 (only one terminal 35 is shown in FIG. 4) to provide electrical current to first wire 36 and second wire 38. A housing 42 defines a cavity 44 therewithin which is sized and adapted to receive and releasably retain dry cell battery 32 to strap 16. For the first exemplary embodiment of expansion indicator device 10 of the present invention, housing 42 is a piece of elastic material 42 connected to strap 16 in a manner whereby the piece of elastic material 42 can stretch open a sufficient amount to form cavity 44 which receives and releasably retains dry cell battery 32 therein. One of ordinary skill in the art would appreciate that other types of housings could be employed by expansion indicator device 10 of the present invention to receive and releasably retain dry cell battery 32 onto strap 16 or user 14 without departing from the inventive spirit hereof.

It is preferred for the expansion indicator device 10 of the present invention that feedback indicator 20 provide a visual indication to user 14 when the threshold amount of stomach cavity expansion has been reached. As best shown in FIGS. 1-4, feedback indicator 20 includes a conventional light bulb 46 and a conventional light bulb socket assembly 48 operative to receive and retain light bulb 46. Now, as illustrated in FIG. 2, when light bulb 46 is energized to the activation state, it illuminates (as shown by dashed lines surrounding light bulb 46), thereby signaling user 14 that the threshold amount of stomach cavity expansion has been reached. And, as illustrated in FIG. 1, when light bulb 46 is de-energized i.e. in the de-activation state or not illuminated, user 14 knows that the threshold amount of stomach cavity expansion has not been achieved. Light bulb socket assembly 48 includes a clip element 49 so that user 14 could secure feedback indicator 20, for example, to his/her shirt sleeve, as shown in FIGS. 1 and 2, or some other support structure for easy viewing. Other conventional clip elements such as an alligator clip could also be utilized.

As shown in FIGS. 1–7, switch assembly 22 includes a band 50 of stiff yet flexible material and a strip 52 of elastic material. Although not by way of limitation, band 50 is formed as a unitary construction with strap 16. Nevertheless, band 50 has a pair of band ends 54 disposed opposite one another and a first electrode 56. First electrode 56 is fastened to an inside band surface 58 of band 50 by a first rivet 57 and is located generally in a center portion thereof. First electrode 56 is electrically connected by wire 36 to feedback indicator 20, which, in turn, is electrically connected by wire 36 to power source 18. Strip 52 of elastic material has a pair of strip ends 60 disposed opposite one another and a second electrode 62. Second electrode 62 is fastened to an inside strip surface 64 of strip 52 by a second rivet 66 and is located generally in a center portion thereof. Second electrode 62 is electrically connected to power source 18 by wire 38. A skilled artisan would appreciate that second electrode 62 could be electrically connected by wire 36 to feedback indicator 20, which, in turn, would be electrically connected by wire 36 to power source 18 and that first electrode 56 could be electrically connected to power source 18 by wire 38.

Figure 6:
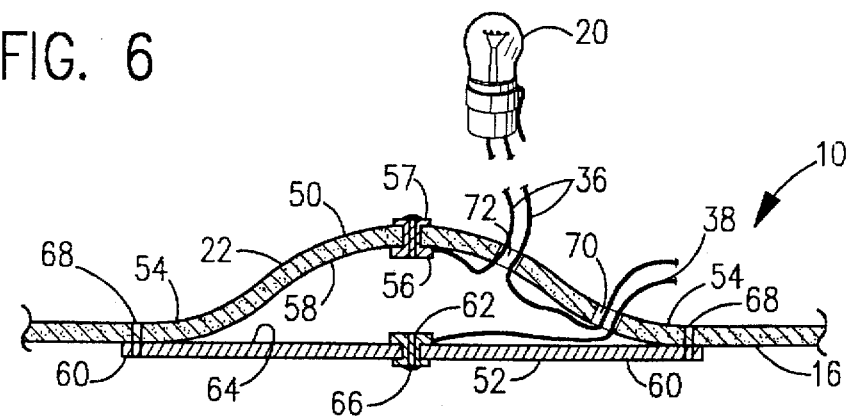
FIG. 6 is a cross-sectional side elevational view of the switch assembly shown in an opened condition.
Figure 7:
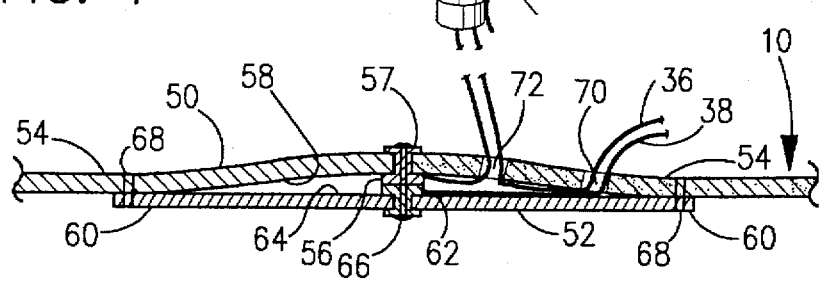
FIG. 7 is a cross-sectional side elevational view of the switch assembly shown in a closed condition.

Band 50 and strip 52 are connected to each other at respective ones of band ends 54 and strip ends 60 by a sewn seam 68. When switch assembly 22 is in the opened condition as best shown in FIG. 6, strip 52 of elastic material is in a relaxed state and band 50 of stiff yet flexible material is in a bowed state thereby separating first and second electrodes 56 and 62 respectfully in a spaced-apart, facially-opposing relationship from one another. When switch assembly 22 is in the closed condition as shown in FIG. 7, strip 52 of elastic material is in a stretched state and band 50 of stiff yet flexible material is in a straightened state thereby causing first and second electrodes 56 and 62 respectfully to contact each other if the threshold amount of stomach cavity expansion is reached.

It is preferred that band 50 is formed with a first hole 70 and a second hole 72 to facilitate wiring of expansion indicator device 10. In FIGS. 4–7, first hole 70 permits wires 36 and 38 to extend between power source 18 and first and second electrodes 56 and 62; second hole 72 permits wire 36 to extend between feedback indicator 20 and first electrode 56.

It is appreciated that switch assembly 22 can be employed for use to electrically connect power source 18 with any electrical element such as feedback indicator 20 when in the closed condition and to electrically disconnect power source 18 from the electrical element when in the opened condition. For example, an opened door relative to the doorjamb can be opened a certain predetermined distance. If the predetermined distance is exceeded, the switch assembly closes to trigger the feedback indicator.

Figure 8:
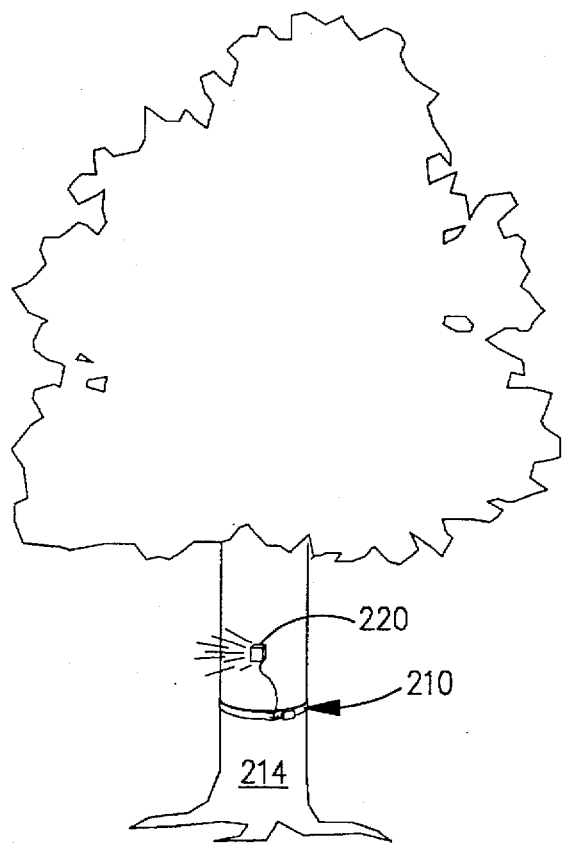
FIG. 8 is a perspective view of the expansion detection device of the present invention being used on an expandable body such as a tree with the feedback indicator such as a buzzer producing sound.

In FIG. 8, an expansion indicator device 210 of a second exemplary embodiment of the present invention is adapted for use around an expandable body 214 such as a tree to indicate whether a threshold amount of body expansion, i.e. growth around a girth of tree 214, is achieved as the body expands. Thus, the expansion indicator device can be used for practically any expandable bodies to determine when a threshold amount of body expansion is achieved. Furthermore, feedback indicator 220 of the second exemplary embodiment of the present invention provides an audible indication when the expandable body reaches its threshold amount of body expansion. Therefore, feedback indicator 220 can be an alarm, a buzzer, a beeper or some other conventional apparatus that upon receiving an electrical signal will produce a sound or noise.

The expansion indicator device of the present invention can be adapted for use around a waist of a user to indicate to the user whether a threshold amount of stomach cavity expansion is achieved as the user breathes or it can be adapted for use around an expandable body to indicate whether a threshold amount of body expansion is achieved as the body expands. The present invention can also be used to determine whether a threshold amount of distance is reached between two bodies linearly separating from each other. Additionally, a user can now monitor his/her own stomach cavity expansion when breathing to determine if adequate breath control is taking place while breathing by merely observing whether the feedback indicator is activated or de-activated. Furthermore, the expansion indicator device employs readily-available, conventional components which leads to inexpensive manufacturing as well as simplicity in design.

Accordingly, the present invention has been described with some degree of particularity directed to the exemplary embodiments of the present invention. It should be appreciated, though, that the present invention is defined by the following claims construed in light of the prior art so that modifications or changes may be made to the exemplary embodiments of the present invention without departing from the inventive concepts contained herein.

I claim:

1. An expansion indicator device adapted for use around a waist of a user to indicate whether a threshold amount of stomach cavity expansion is achieved as the user breathes, comprising:

(a) a strap fabricated from a stiff yet flexible material, said strap sized and adapted to be secured around the waist of the user;

(b) a power source;

(c) a feedback indicator operative between an activation state whereby said power source is connected to said feedback indicator thereby energizing said feedback indicator and a deactivation state whereby said power source is disconnected from said feedback indicator thereby de-energizing said feedback indicator; and (d) a switch assembly interconnected to said power source and said feedback indicator and operatively connected to said strap so that, as the user breathes, said switch assembly is operative to move between a closed condition whereby, when the threshold amount of stomach cavity expansion is reached, said feedback indicator becomes energized to the activation state and an open condition whereby, when the amount of stomach cavity expansion falls below the threshold amount, said feedback indicator becomes de-energized to the deactivation state;

said switch assembly including a band of stiff yet flexible material having a pair of band ends disposed opposite one another and a first electrode fastened to said band and electrically connected to one of said power source and said feedback indicator and a strip of elastic material having a pair of strip ends disposed opposite one another and a second electrode fastened to said strip and electrically connected to a remaining one of said power source and said feedback indicator, said band and said strip connected to each other at respective ones of said band ends and strip ends so that, when said switch assembly is in the opened condition, said strip is in a relaxed state and said band is in a bowed state thereby separating said first and second electrodes in a spaced-apart, facially-opposing relationship from one another and, when said switch is in said closed condition, said strip is in a stretched state and said band is in a straightened state thereby causing said first and second electrodes to contact each other.

2. An expansion indicator device according to claim 1 wherein said strap includes a first free end portion and a second free end portion, said first and second free end portions adapted to releasably fasten to one another.

3. An expansion indicator device according to claim 2 wherein said said first free end portion includes one of a hook fastener and a loop fastener and wherein said second free end portion includes a remaining one of said hook fastener and said loop fastener.

4. An expansion indicator device according to claim 1 wherein said stiff yet flexible material is selected from a group consisting of cloth, nylon, leather, imitation leather and plastic.

5. An expansion indicator device according to claim 1 wherein said power source includes a dry cell battery.

6. An expansion indicator device according to claim 5 including a housing defining a cavity therein sized and adapted to retain said dry cell battery.

7. An expansion indicator device according to claim 6 wherein said housing is operative to be releasably connected to said strap.

8. An expansion indicator device according to claim 1 wherein said feedback indicator provides a visual indication.

9. An expansion indicator device according to claim 1 wherein said feedback indicator provides an audible indication.

10. An expansion indicator device according to claim 1 wherein said feedback indicator is selected from a group consisting of a light bulb, an alarm, a buzzer and a beeper.

11. An expansion indicator device adapted for use around an expandable body to indicate whether a threshold amount of body expansion is achieved as the body expands, comprising:

(a) a strap fabricated from a stiff yet flexible material, sized and adapted to be secured around the expandable body;

(b) a power source;

(c) a feedback indicator operative between an activation state whereby said power source is connected to said feedback indicator thereby energizing said feedback indicator and a de-activation state whereby said power source is disconnected from said feedback indicator thereby de-energizing said feedback indicator; and (d) a switch assembly interconnected to said power source and said feedback indicator and connected to and operative with said strap so that, as the body expands, said switch assembly is operative to move between a closed condition whereby, when the threshold amount of body expansion is reached, said feedback indicator becomes energized to the activation state and an open condition whereby, when the amount of stomach cavity expansion falls below the threshold amount, said feedback indicator becomes de-energized to the deactivation state;

said switch assembly including a band of stiff yet flexible material having a pair of band ends disposed opposite one another and a first electrode fastened to said band and electrically connected to one of said power source and said feedback indicator and a strip of elastic material having a pair of strip ends disposed opposite one another and a second electrode fastened to said strip and electrically connected to a remaining one of said power source and said feedback indicator, said band and said strip connected to each other at respective ones of said band ends and strip ends so that, when said switch assembly is in the opened condition, said strip is in a relaxed state and said band is in a bowed state thereby separating said first and second electrodes in a spaced-apart, facially-opposing relationship from one another and, when said switch is in said closed condition, said strip is in a stretched state and said band is in a straightened state thereby causing said first and second electrodes to contact each other.

12. An expansion indicator device according to claim 11 wherein said power source includes a dry cell battery.

13. An expansion indicator device according to claim 12 including a holder sized and adapted to retain said dry cell battery.

14. An expansion indicator device according to claim 11 wherein said feedback indicator is selected from a group consisting of a light bulb, an alarm, a buzzer and a beeper.

* * * * *